United States Patent
Imamura et al.

(10) Patent No.: US 10,687,837 B2
(45) Date of Patent: Jun. 23, 2020

(54) METHOD FOR MANUFACTURING MEDICAL BASKET TREATMENT TOOL AND THE MEDICAL BASKET TREATMENT TOOL

(71) Applicant: OLYMPUS CORPORATION, Hachioji-shi, Tokyo (JP)

(72) Inventors: Tomonori Imamura, Tokyo (JP); Jumpei Otake, Tokyo (JP); Takeshi Hidaka, Tokyo (JP); Kazuaki Uchida, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 242 days.

(21) Appl. No.: 15/907,609

(22) Filed: Feb. 28, 2018

(65) Prior Publication Data
US 2018/0185042 A1    Jul. 5, 2018

Related U.S. Application Data (63) Continuation of application No. PCT/JP2016/073755, filed on Aug. 12, 2016.

(30) Foreign Application Priority Data

Sep. 3, 2015 (JP) ................ 2015-174063

(51) Int. Cl.
*A61B 17/22* (2006.01)
*A61B 17/221* (2006.01)
(Continued)

(52) U.S. Cl.
CPC ............. *A61B 17/221* (2013.01); *C21D 1/26* (2013.01); *C21D 6/004* (2013.01); *C22F 1/006* (2013.01);
(Continued)

(58) Field of Classification Search
CPC . A61B 17/22; A61B 17/221; A61B 17/32056; A61B 17/22004;
(Continued)

(56) References Cited

U.S. PATENT DOCUMENTS 5,208,434 A    5/1993  Minamida et al.
5,906,622 A *  5/1999  Lippitt ................ A61B 17/221
                                                  606/113

(Continued)

FOREIGN PATENT DOCUMENTS

JP        04280915 A      10/1992
JP        10165406 A       6/1998
(Continued)

OTHER PUBLICATIONS

International Search Report (ISR) dated Oct. 18, 2016 issued in International Application No. PCT/JP2016/073755.
(Continued)

*Primary Examiner* — Vi X Nguyen
(74) *Attorney, Agent, or Firm* — Holtz, Holtz & Volek PC (57) ABSTRACT

The present invention provides a method for manufacturing a medical basket treatment tool. The method for manufacturing a medical basket treatment tool having one or more wire formed using an alloy containing two or more metals includes a heating process of performing heat treatment on a target portion of at least one wire among the wires one or more times, the heat treatment irradiating the target portion with a laser with an irradiation fluence of $10^3$ J/cm$^2$ or more and heating the target portion to become a predetermined temperature lower than the solid solubility limit of the alloy.

6 Claims, 8 Drawing Sheets

(51) Int. Cl.
*C22F 1/10* (2006.01)
*C21D 6/00* (2006.01)
*C21D 1/26* (2006.01)
*C22F 1/00* (2006.01)
*C21D 1/09* (2006.01)
*A61B 90/00* (2016.01)
*A61B 17/00* (2006.01)

(52) U.S. Cl.
CPC ...... *C22F 1/10* (2013.01); *A61B 2017/00526* (2013.01); *A61B 2017/00867* (2013.01); *A61B 2017/2212* (2013.01); *A61B 2090/037* (2016.02); *C21D 1/09* (2013.01)

(58) Field of Classification Search
CPC ....... A61B 17/22031; A61B 2017/2212; A61B 2017/2215
See application file for complete search history.

(56) References Cited

U.S. PATENT DOCUMENTS

| | | | |
|---|---|---|---|
| 6,048,342 | A | 4/2000 | Zucherman et al. |
| 6,673,080 | B2 | 1/2004 | Reynolds et al. |
| 7,645,283 | B2 | 1/2010 | Reynolds et al. |
| 8,562,624 | B2 * | 10/2013 | Uihlein ................ A61B 17/221 606/127 |
| 2002/0055712 | A1 | 5/2002 | Neracher |
| 2004/0138677 | A1 | 7/2004 | Little et al. |
| 2005/0276718 | A1 | 12/2005 | Burgermeister et al. |
| 2009/0018469 | A1 | 1/2009 | Yanuma et al. |
| 2010/0106164 | A1 | 4/2010 | Reynolds et al. |

FOREIGN PATENT DOCUMENTS

| | | |
|---|---|---|
| JP | 2002012916 A | 1/2002 |
| JP | 2003518415 A | 6/2003 |
| JP | 2003523214 A | 8/2003 |
| JP | 2006006926 A | 1/2006 |
| JP | 2006122969 A | 5/2006 |
| JP | 2009018160 A | 1/2009 |
| JP | 4226327 B2 | 2/2009 |
| JP | 2013000219 A | 1/2013 |
| WO | 9921501 A1 | 5/1999 |
| WO | 0147586 A1 | 7/2001 |

OTHER PUBLICATIONS

Written Opinion dated Oct. 18, 2016 issued in International Application No. PCT/JP2016/073755.

* cited by examiner

METHOD FOR MANUFACTURING MEDICAL BASKET TREATMENT TOOL AND THE MEDICAL BASKET TREATMENT TOOL

This application is a continuation application based on a PCT Patent Application No. PCT/JP2016/073755, filed on Aug. 12, 2016, whose priority is claimed on Japanese Patent Application No. 2015-174063, filed on Sep. 3, 2015, the content of which are incorporated herein by reference.

TECHNICAL FIELD

The present invention relates to a method for manufacturing a medical basket treatment tool and a medical basket treatment tool.

BACKGROUND ART

Conventionally, a medical basket is known as a medical device that is trans endoscopically inserted into a body lumen and grasps a foreign material (a collected material) such as a calculus generated in the body lumen such as a bile duct. The medical basket generally includes a manipulating wire that is retractably inserted into a sheath having a long tube shape, and a basket unit that is provided at a distal end of the manipulating wire. The basket unit is made of a plurality of wires. A tip is fastened through a swaging process or the like, and thereby front ends of the plurality of wires are bundled. Rear ends of the plurality of wires are bundled by a connecting member, and are connected to the manipulating wire via the connecting member. When the foreign material is collected by the medical basket, the foreign material is grasped by the plurality of wires of the basket unit, and is removed from the body. However, in the medical basket, for example when the collected material is extremely large, if the basket unit is pulled into the sheath with the foreign material grasped, the foreign material cannot be collected because of impaction. Furthermore, in this case, the foreign material may not be detached from the wires of the basket unit. In the medical basket, when the foreign material causes impaction in this way, to prevent a need to perform a laparotomy, a mechanism capable of releasing the foreign material from the wires of the basket unit is proposed.

For example, in Japanese Patent No. 4226327 discloses a medical device having a handle, a sheath that is provided to extend from the handle in a distal direction and has a lumen extending from a distal end to a proximal end, a traction member that is disposed in the lumen of the sheath in an axial direction, and a basket that is connected to a distal end of the traction member. The basket of the medical device includes a plurality of wires, and a tip joint that is disposed at a distal end of the basket. Ends of the plurality of wires are fixed to the tip joint. This tip joint is configured to be deformed by a force smaller than a force that is required to break down the traction member or at least one of the wires of the basket, and the ends of the plurality of wires are configured to be removed from the tip joint. Thereby, in this medical device, when the foreign material causes impaction, the tip joint is deformed and separated from the wires, and the bundling of the wires is released. Thereby, the foreign material can be released from the basket. However, in this case, after the ends of the wires are removed from the tip joint, the tip joint remains in the body of the patient, and thus there is a need to perform another treatment in order to recover the tip joint.

In contrast, in Japanese Unexamined Patent Application, First Publication No. 2013-219 discloses a medical basket type treatment device having a manipulating wire that is disposed in a tubular sheath, a basket unit that is connected to a distal portion of the manipulating wire, and a distal end tip which is provided at a distal portion of the basket unit and bundles distal portions of a plurality of basket wires constituting the basket unit. This distal end tip has a fragile part with weaker strength than other portions of the distal end tip. When a force greater than or equal to a predetermined force is applied to the manipulating wire, the distal end tip is configured to be divided at the fragile part without breaking the manipulating wire. In this medical basket type treatment device, when the basket wires grasp the foreign material and impaction occurs, the manipulating wire is pulled to a proximal side. Thereby, when a force greater than or equal to a predetermined force acts on the manipulating wire and the basket wires, the manipulating wire or the basket wires are not broken, the distal end tip is broken into two pieces at the fragile part, and the foreign material can be released from the basket wires. In the medical basket type treatment device, even when the distal end tip is broken into the two pieces, each of the divided distal end tips is connected to the basket wires, and thus the distal end tip can be prevented from remaining in the body of the patient.

In Japanese Unexamined Patent Application, First Publication No. H10-165406 discloses a wire loop type treatment tool for an endoscope in which a plurality of elastic wires, which are integrally bundled at front and rear end sides and form loops, are coupled to a front end of a manipulating wire. In this treatment tool, distal end portions of the plurality of elastic wires are not bundled by another member, and are mutually joined by joining means such as soldering, brazing, or welding, and thereby are integrally bundled. In this treatment tool, a length of a joint of the front ends of the elastic wires is made to be shorter than that of a joint of the rear end sides of the elastic wires and that of a joint of the front end of the manipulating wire, and thereby junction of the front portions of the elastic wires is configured to be necessarily broken when an excessive force is applied to the elastic wires. In this treatment tool, when the elastic wires grasp the foreign material and impaction occurs, the junction of the front portions of the elastic wires is broken, and the foreign material can be released from the elastic wires. In this treatment tool, since the front portions of the plurality of elastic wires are bundled without using a distal end tip, the distal end tip does not remain in the body of the patient.

SUMMARY OF INVENTION

According to a first aspect of the present invention, a method for manufacturing a medical basket treatment tool is a method for manufacturing a medical basket treatment tool having one or more wire formed using an alloy containing two or more metals, and includes a heating process of performing heat treatment, which irradiates a target portion of at least one wire among the wires with a laser with an irradiation fluence of $10^3$ J/cm$^2$ or more and heats the target portion to become a predetermined temperature lower than a solid solubility limit of the alloy, on the target portion one or more times.

According to a second aspect of the present invention, in the method for manufacturing a medical basket treatment tool of the first aspect, the heat treatment may be performed in a gas atmosphere.

According to a third aspect of the present invention, in the method for manufacturing a medical basket treatment tool of the first aspect, the alloy may be a shape-memory alloy containing Ni at 55.8 wt % or more and 56.0 wt % or less.

According to a fourth aspect of the present invention, in the method for manufacturing a medical basket treatment tool of the third aspect, the predetermined temperature of the heat treatment may be 550° C. or higher and 800° C. or lower.

According to a fifth aspect of the present invention, in the method for manufacturing a medical basket treatment tool of the first aspect, the alloy may be stainless steel containing Cr at 16 wt % or more and 26 wt % or less and Ni at 4 wt % or more and 26 wt % or less.

According to a sixth aspect of the present invention, in the method for manufacturing a medical basket treatment tool of the fifth aspect, the predetermined temperature of the heat treatment may be 600° C. or higher and 1000° C. or lower.

According to a seventh aspect of the present invention, a medical basket treatment tool is a medical basket treatment tool having one or more wire formed using an alloy containing two or more metals, and includes at least one wire among the wires has a fragile part subjected to thermal embrittlement in a part of its a lengthwise direction, and the fragile part is the same exterior as the other part of the wire.

According to an eighth aspect of the present invention, in the medical basket treatment tool of the seventh aspect, the fragile part may be formed by irradiating a target portion of the at least one wire with a laser with an irradiation fluence of $10^3$ J/cm$^2$ or more and heating the target portion to become a predetermined temperature lower than a solid solubility limit of the alloy.

DESCRIPTION OF EMBODIMENTS

Hereinafter, an embodiment of the present invention will be described with reference to FIG. 1 to FIG. 13.

Figure 1:
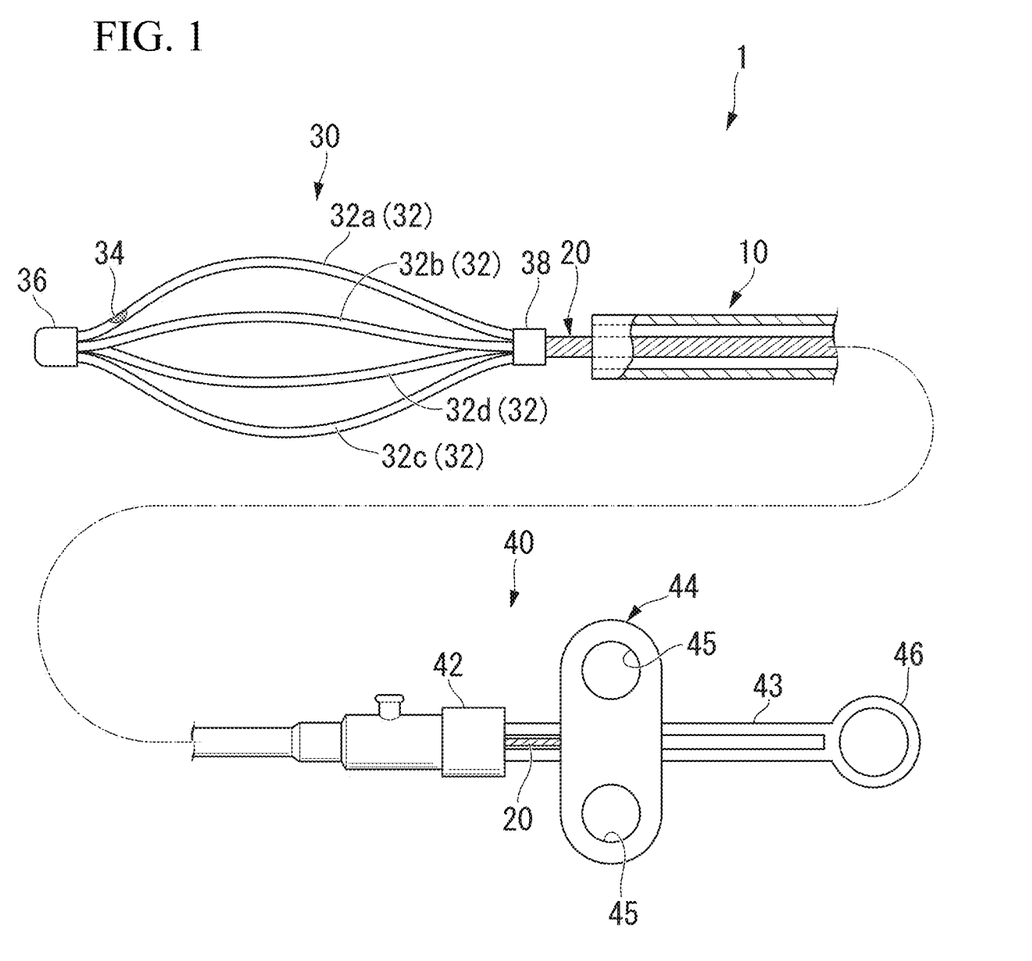
FIG. 1 is a view showing a medical basket treatment tool according to an embodiment of the present invention.

FIG. 1 is a view showing a medical basket 1 that is a medical basket treatment tool according to an embodiment of the present invention. The medical basket 1 includes a sheath 10 having flexibility, a manipulating wire 20 that is retractably inserted into the sheath 10, a basket unit 30 that is provided at a distal end of the manipulating wire 20, and a manipulator 40 that is provided at a proximal end of the sheath 10 and can be manipulated to advance/retract the manipulating wire 20. The sheath 10 is formed to extend in an axial direction, and can be inserted into a treatment tool channel of an endoscope. The distal end of the manipulating wire 20 is coupled to the basket unit 30, and a proximal end of the manipulating wire 20 is coupled to the manipulator 40.

The basket unit 30 is made up of basket wires 32, each of which has elasticity. In the present embodiment, the basket unit 30 is made up of four basket wires 32a, 32b, 32c and 32d. The number of basket wires is an example, and is not limited to this. A distal end tip 36 is provided at the distal end of the basket unit 30. Distal ends of the basket wires 32a, 32b, 32c and 32d are coupled to the distal end tip 36, and distal ends of the basket wires 32a, 32b, 32c and 32d are bundled by the distal end tip 36. A bundling member 38 is provided at a proximal end of the basket unit 30. Proximal ends of the basket wires 32a, 32b, 32c and 32d are coupled to a distal end side of the bundling member 38, and proximal ends of the basket wires 32a, 32b, 32c and 32d are bundled by the bundling member 38. A proximal end side of the bundling member 38 is coupled to the distal end of the manipulating wire 20.

The basket wires 32a, 32b, 32c and 32d are habit-shaped so that the basket unit 30 spreads into a basket shape as a whole. A fragile part 34 that is configured to be more easily broken than other parts is formed on the basket wire 32 by a heating process to be described below. In an example shown in FIG. 1, the fragile part 34 is formed on the basket wire 32a, and is disposed at a position that is closer to the distal end of the basket unit 30 than the proximal end of the basket unit 30. When the basket unit 30 grasps a foreign material and then impaction occurs and an excessive force is applied, this fragile part 34 is broken, and thereby the foreign material is released from the basket unit 30. A plurality of fragile parts 34 may be provided. In this case, in addition to the basket wire 32a, the fragile part 34 may be formed on the other basket wires (e.g., the basket wire 32b).

Each of the basket wires 32 is formed using an alloy containing two or more metals. As this alloy, for example, a shape-memory alloy such as NiTi containing Ni at 55.8 wt % or more and 56.0 wt % or less, or stainless steel containing Cr at 16 wt % or more and 26 wt % or less and Ni at 4 wt % or more and 26 wt % or less may be used.

The basket unit 30 is advanced into the sheath 10 in association with advancing/retracting movement of the manipulating wire 20, and can be advanced/retracted in the sheath 10. For this reason, the distal end tip 36 has an outer diameter smaller than an inner diameter of the sheath 10. Likewise, the bundling member 38 has an outer diameter smaller than the inner diameter of the sheath 10. When the basket unit 30 is advanced into the sheath 10, the basket wires 32a, 32b, 32c and 32d are elastically deformed to be contracted in a radial direction.

The manipulator 40 includes a manipulator main body 42 coupled to the proximal end of the sheath 10, and a slider 44 that can be advanced/retracted with respect to the manipulator main body 42 in a longitudinal direction. A slider receiving part 43 extending in a longitudinal direction is provided at the manipulator main body 42. A finger hooking part 46 is provided at a proximal end of the slider receiving part 43. The slider 44 is provided to be slidable on the slider receiving part 43 in a longitudinal direction. Finger hooking parts 45 are provided at the slider 44. An insertion hole (not shown) communicating with an lumen of the sheath 10 is formed in the manipulator main body 42, and the proximal end of the manipulating wire 20 passes through this insertion hole and is coupled to the slider 44. Therefore, the slider 44 is advanced/retracted in the manipulator 40 in a longitudinal direction. Thereby, the manipulating wire 20 can be advanced/retracted in the sheath 10 in an axial direction. Accordingly, the basket unit 30 is advanced/retracted.

The sheath 10, the manipulating wire 20, and the manipulator 40 are not limited to the above constitution, and a known constitution may be adopted.

Next, with regard to a method for manufacturing a medical basket treatment tool according to an embodiment of the present invention, a method for manufacturing the fragile part 34 will be mainly described using the medical basket 1 as an example.

A method for manufacturing a medical basket treatment tool according to the present embodiment includes a heating process. The heating process is a process of performing heat treatment of heating a target portion of at least one wire on the target portion one or more times to irradiate the target portion with a laser with an irradiation fluence of $10^3$ J/cm$^2$ or more to become a predetermined temperature lower than a solid solubility limit of an alloy of which the wire is formed. In the method for manufacturing a medical basket treatment tool according to the present embodiment, since mechanical strength (e.g., tensile strength) of the target portion can be properly reduced by this heating process, the target portion can be reliably broken when an excessive force is applied. The fragile part 34 of the medical basket 1 is formed in this heating process, and the target portion subjected to the heat treatment becomes the fragile part 34.

Figure 2:
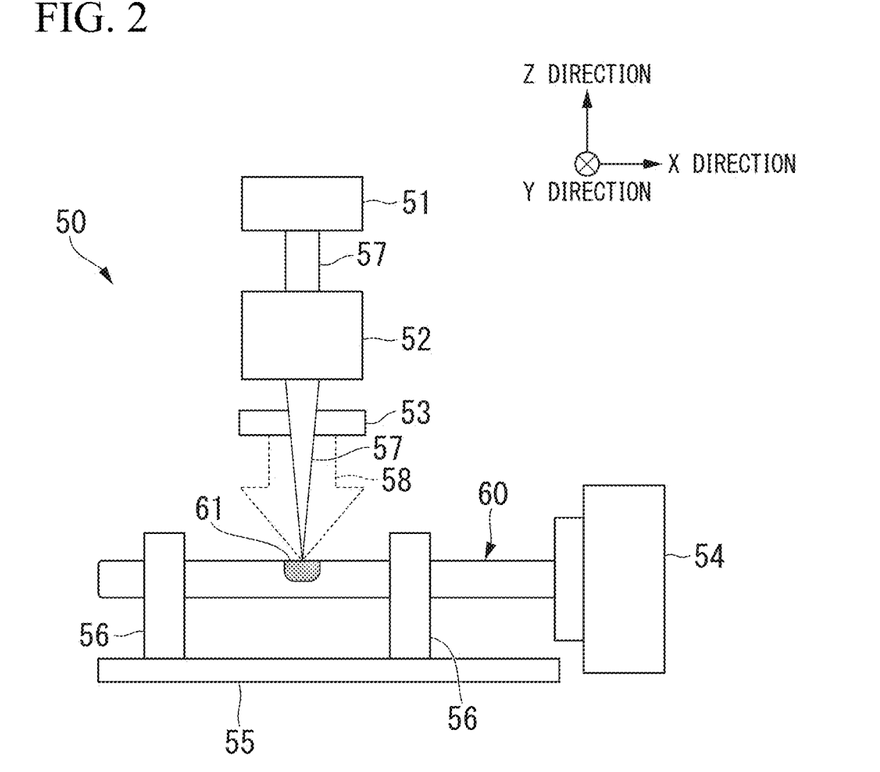
FIG. 2 is a view showing a laser heat treatment apparatus used in a heating process in the method for manufacturing a medical basket treatment tool according to the embodiment of the present invention.

FIG. 2 is a view showing a laser heat treatment apparatus 50 used in the heating process in the method for manufacturing a medical basket treatment tool according to the embodiment of the present invention. The heating process is performed using the laser heat treatment apparatus 50. The laser heat treatment apparatus 50 includes a laser generator 51, an optical head 52, a gas injector 53, a holder 54, and a stage 55. The laser generator 51 generates a laser 57 having predetermined power. The wavelength of the laser 57 is, for instance, 800 to 1100 nm. The optical head 52 includes a condensing lens (not shown), and adjusts the irradiation position, the area of an irradiation surface, and so on, of the laser 57 on a wire 60. The gas injector 53 injects a gas 58 such as argon gas or nitrogen gas toward a target portion 61 of the wire 60. The holder 54 holds the wire 60 to be subjected to the heating process. The stage 55 includes supports 56 on the top thereof, and supports the wire 60 held by the holder 54 using the supports 56. In the laser heat treatment apparatus 50, when the laser is irradiated in a Z direction among the mutually orthogonal X direction, Y direction, and Z direction that are shown in FIG. 2, the stage 55 may be configured to be movable relative to the optical head 52 in each of the X direction, the Y direction, and the Z direction along with the holder 54 that supports the wire 60. Further, the wire 60 supported by the supports 56 held by the holder 54 is not limited to one formed in a linear shape, and may be one having a complicated shape like a basket. In this case, the holder 54 and the supports 56 may be configured to be able to hold a wire having a complicated shape.

Next, performing procedures of the heating process will be described using a case in which the heat treatment is performed on the target portion 61 of the wire 60 as an example. Like the basket wires 32 of the medical basket 1, the wire 60 is formed using an alloy containing two or more metals. In the heating process, first, the wire 60 is supported by the supports 56 on the stage 55 while being held by the holder 54, and a position of the wire 60 is fixed. Subsequently, the optical head 52 is adjusted such that the laser 57 is radiated on the target portion 61 of the wire 60. Further, the laser generator 51 and the optical head 52 are adjusted such that the irradiation fluence reaches a predetermined value of $10^3$ J/cm$^2$ or more. Here, the irradiation fluence is obtained by the following formula.

$$\text{Irradiation fluence [J/cm}^2\text{]} = \tag{1}$$
$$\text{Power per unit area of laser irradiation surface [W/cm}^2\text{]} \times$$
$$\text{Irradiation time [s]} = \text{Laser power [W]/Area of}$$
$$\text{laser irradiation surface [cm}^2\text{]} \times \text{Irradiation time [s]}$$

$$\text{Area of laser irradiation surface [cm}^2\text{]} = \tag{2}$$
$$\pi \times (\text{Spot diameter of laser [cm]})^2/4$$

That is, the irradiation fluence can be adjusted by appropriately changing the laser power, the area of the laser irradiation surface, and the irradiation time. The degree of reduction of the tensile strength of the target portion 61 can be adjusted by adjusting the irradiation fluence.

After the above adjustment is completed, the laser 57 is irradiated from the laser generator 51 to the target portion 61 while the gas 58 is injected from the gas injector 53 toward the target portion 61. Thereby, the target portion 61 is heated. Afterward, the irradiation of the laser 57 is stopped when a predetermined irradiation time has elapsed, and the heat treatment for the target portion 61 is completed. In this heat treatment, when the target portion 61 is heated to a temperature that exceeds the solid solubility limit of the alloy of which the wire 60 is formed, the target portion 61 may melt. For this reason, in this heat treatment, the irradiation fluence (the laser power, the irradiation time, etc.) needs to be appropriately adjusted such that the target portion 61 is heated to a predetermined temperature lower than the solid solubility limit of the alloy. This heat treatment is performed on the target portion 61 one or more times, and thereby the heating process is performed.

When the range of the target portion 61 of the wire 60 is wide or when the heat treatment is performed on a plurality of target portions 61, the stage 55 and the holder 54 are properly displaced in the X direction, the Y direction, and the Z direction, and thereby the heat treatment can be performed on the target portion 61 having a desired shape. In the laser heat treatment apparatus 50, the optical head 52 may be configured to be movable relative to the stage 55 and the holder 54.

The method for manufacturing a medical basket treatment tool according to the present embodiment further includes a basket forming process. The basket forming process is a process of forming the medical basket 1 using the wire 60 having the target portion 61. Thereby, the wire 60 having the target portion 61 is used as the basket wire 32, and the medical basket 1 in which the target portion 61 on which the heat treatment is performed is used as the fragile part 34 can be formed.

The basket forming process may not be necessarily performed after the heating process is performed. After the basket forming process is performed first and the basket unit 30 is formed using the wire 60, the heating process may be performed. The laser heat treatment apparatus 50 may be configured to enable the optical head 52 to move in the X direction, the Y direction, and the Z direction, and to rotate around the X axis, the Y axis, and the Z axis such that the optical head 52 does not interfere with the wire having a complicated shape like the basket unit 30 when this wire is disposed on the stage 55. Thereby, the laser heat treatment apparatus 50 can appropriately adjust the position and direction of the optical head 52, and can accurately irradiate the target portion of the wire with the laser.

Typically, since the target portion subjected to the heat treatment by the aforementioned heating process and other portions not subjected to heat treatment in the wire are different in structure, but are not different in exterior, they cannot be distinguished by sight. Therefore, when the basket unit is formed using the wire after the heating process is performed, the target portion subjected to the heat treatment, namely the fragile part, may be disposed at an incorrect position. For this reason, in the method for manufacturing a medical basket treatment tool according to the present embodiment, the heating process is preferably performed after the basket unit is formed using the wire. In the aforementioned heating process, since the heat treatment is performed using the laser, the target portion can be heated by properly adjusting an optical path of the laser even in a place in which the target portion cannot be locally heated by different heating means in the complicated shape like the basket unit. Therefore, in the method for manufacturing a medical basket treatment tool according to the present embodiment, even when the heating process is performed after the basket unit is formed, the heat treatment can be properly performed on the target portion.

As described above, the heating process and the basket forming process are performed in the method for manufacturing a medical basket treatment tool according to the present embodiment, and thereby the medical basket 1 having the fragile part 34 can be formed.

In the aforementioned heating process, the predetermined temperature in the heat treatment is, for instance, the following value. As an example, when the alloy of which the wire 60 is formed is a shape-memory alloy containing Ni at 55.8 wt % or more and 56.0 wt % or less, the predetermined temperature in the heat treatment is preferably 550° C. or higher and 800° C. or lower. In the heating process, the irradiation fluence is adjusted to perform the heat treatment such that the target portion 61 is heated to a temperature within this temperature range, and thereby the tensile strength of the wire 60 can be favorably reduced.

As another example, when the alloy of which the wire 60 is formed is stainless steel containing Cr at 16 wt % or more and 26 wt % or less and Ni at 4 wt % or more and 26 wt % or less, the predetermined temperature in the heat treatment is preferably 600° C. or higher and 1000° C. or lower. In the heating process, the irradiation fluence is adjusted to perform the heat treatment such that the target portion 61 is heated at a temperature within this temperature range, and thereby the tensile strength of the wire 60 can be favorably reduced.

Figure 3:
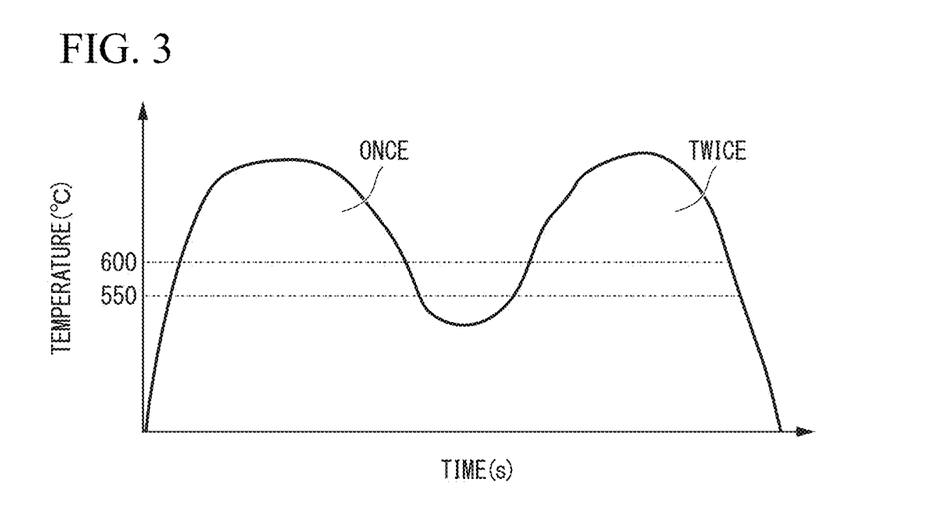
FIG. 3 is a view showing an example of a heat history in the heating process of the method for manufacturing a medical basket treatment tool according to the embodiment of the present invention.

In the aforementioned heating process, the heat treatment performed on the target portion 61 may be performed two or more times. The number of heat treatments can be counted as once whenever the target portion 61 exceeds the predetermined temperature in the heat treatment. FIG. 3 shows a heat history in the heating process of the method for manufacturing a medical basket treatment tool according to the embodiment of the present invention. As shown in FIG. 3, for example, if the predetermined temperature is set to 550° C. when the alloy of which the wire 60 is formed is the aforementioned shape-memory alloy containing Ni, the temperature of the target portion 61 exceeds 550° C., then becomes lower than 550° C., and then exceeds 550° C. again. Therefore, in this case, the heat treatment is performed twice. When the predetermined temperature is set to 600° C. when the alloy of which the wire 60 is formed is the aforementioned stainless steel, the heat treatment is likewise performed twice.

The aforementioned basket forming process is not an essential constitution, and thus the method for manufacturing a medical basket treatment tool of the present invention may not include the basket forming process.

Next, with regard to a motion of the medical basket 1 when in use, a motion of the fragile part 34 when broken will be mainly described.

Figure 4:
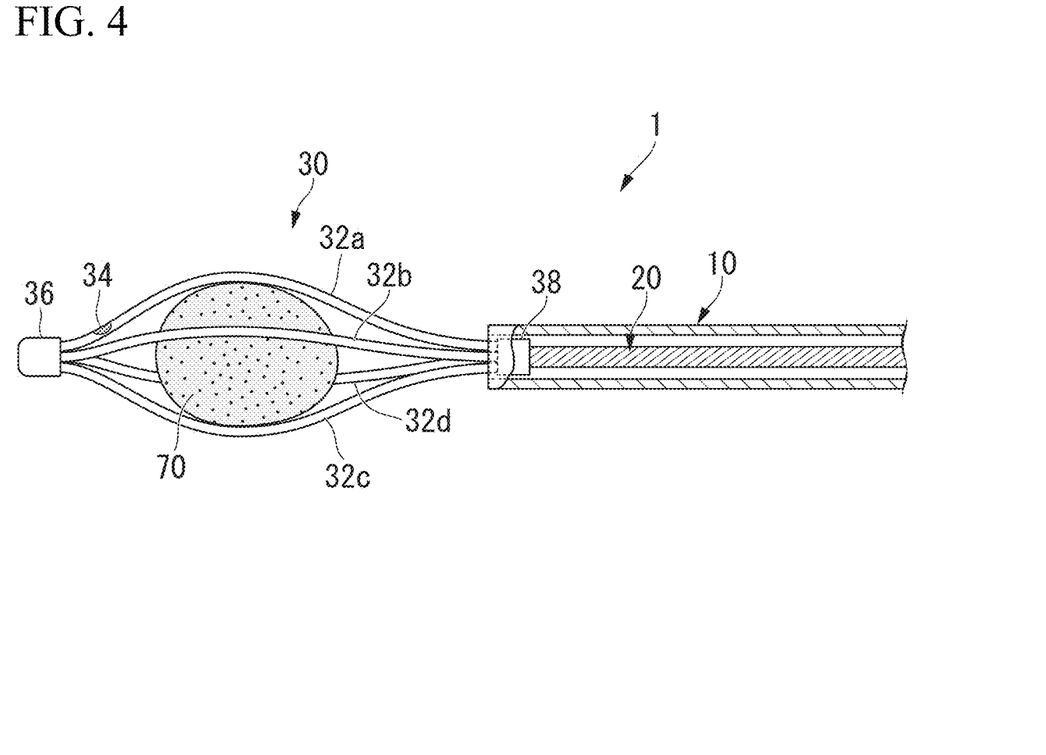
FIG. 4 is a view showing a motion of the medical basket treatment tool according to an embodiment of the present invention when in use.
Figure 5:
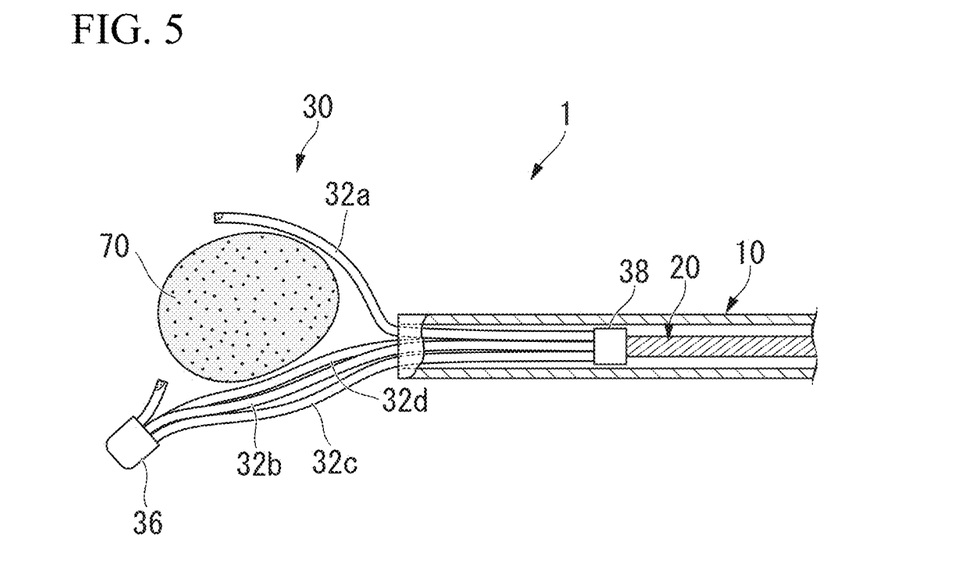
FIG. 5 is a view showing a motion of the medical basket treatment tool according to the embodiment of the present invention when in use.

FIG. 4 and FIG. 5 are views showing a motion of the medical basket 1 when in use. FIG. 4 shows a state in which a foreign material 70 impacts the medical basket 1 and the foreign material 70 is not detached. In this state, when the manipulating wire 20 is pulled to the proximal end side and a force greater than or equal to predetermined tensile strength is applied to the basket unit 30, the fragile part 34 configured to be more easily broken than other parts by the heat treatment of the heating process is broken at the basket wire 32a as shown in FIG. 5. Thereby, the foreign material 70 is released from the basket unit 30. At this time, since the distal end tip 36 is still coupled to the basket wires 32b, 32c and 32d, the distal end tip 36 is not left in the body of the patient. The fragile part 34 is provided in the vicinity of the distal end tip 36 (at a position closer to the distal end of the basket unit 30 than the proximal end of the basket unit 30). Thereby, since the length of a portion coupled to the distal end tip 36 of the broken basket wire 32a becomes short, surrounding tissue can be prevented from being damaged by a broken end of this portion.

Figure 6:
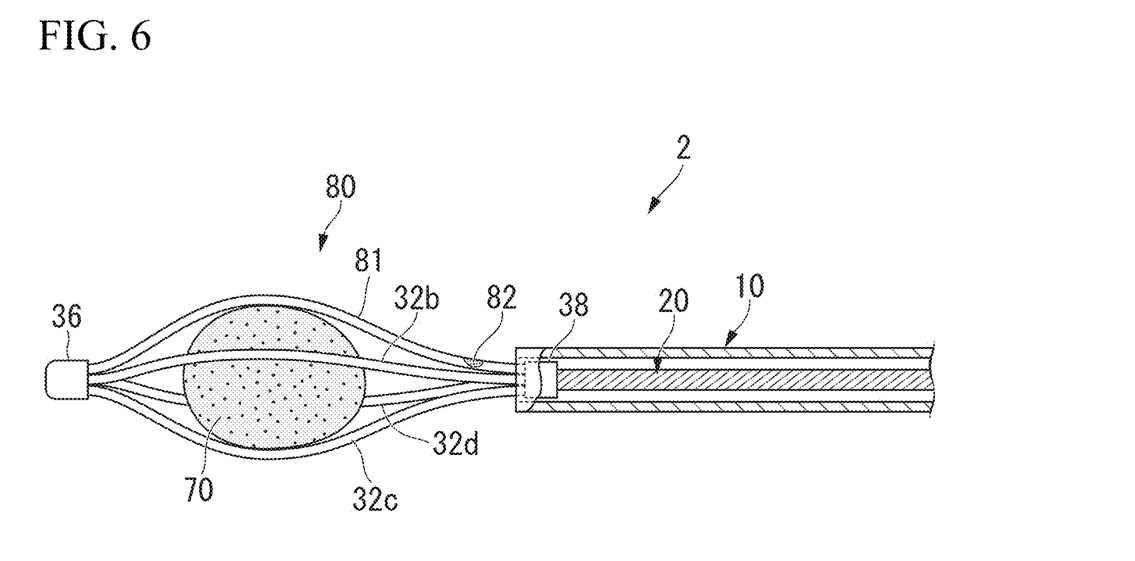
FIG. 6 is a view showing a motion of a first modification of the medical basket treatment tool according to the embodiment of the present invention when in use.
Figure 7:
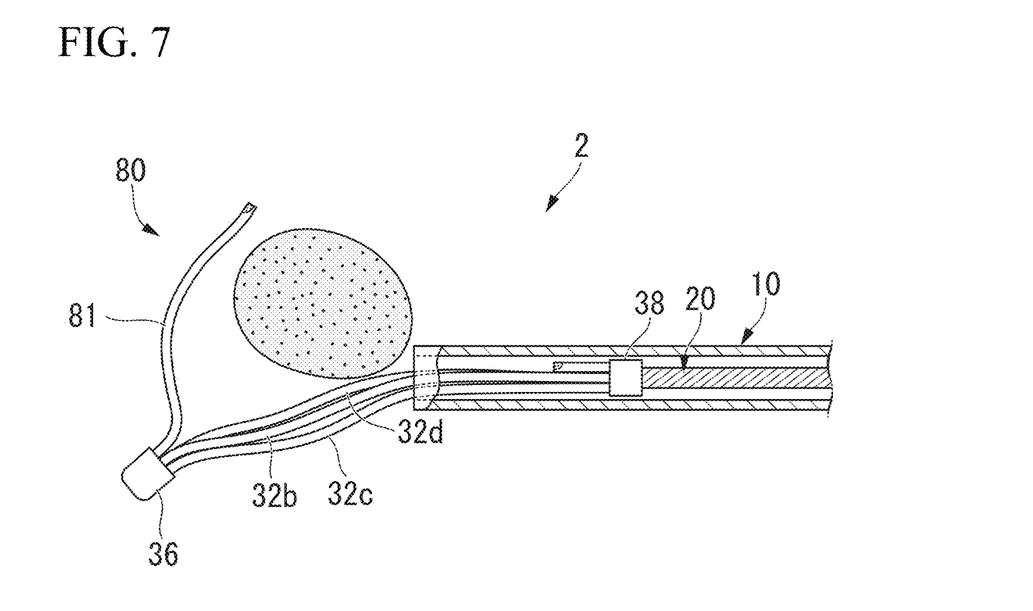
FIG. 7 is a view showing the motion of the first modification of the medical basket treatment tool according to the embodiment of the present invention when in use.

As a first modification of the medical basket treatment tool according to the present embodiment, a medical basket 2 is shown in FIG. 6 and FIG. 7. The medical basket 2 is different from the medical basket 1 in that, in place of the fragile part 34, a fragile part 82 is provided in the vicinity of the bundling member 38 (at a position closer to a proximal end of a basket unit 80 than a distal end of the basket unit 80) on a basket wire 81. With regard to other constitutions, the medical basket 2 has the same constitution as the medical basket 1.

FIG. 6 and FIG. 7 are views showing a motion of the medical basket 2 when in use. FIG. 6 shows a state in which a foreign material 70 impacts the medical basket 2 and the foreign material 70 is not detached. In this state, when the manipulating wire 20 is pulled to the proximal end side and a force greater than or equal to predetermined tensile strength is applied to the basket unit 80, the fragile part 82 configured to be more easily broken than other parts by the heat treatment of the heating process is broken at the basket wire 81 as shown in FIG. 7. Thereby, the foreign material 70 is released from the basket unit 80. At this time, since the distal end tip 36 is still coupled to the basket wires 32b, 32c and 32d, the distal end tip 36 is not left in the body of the patient.

Figure 8:
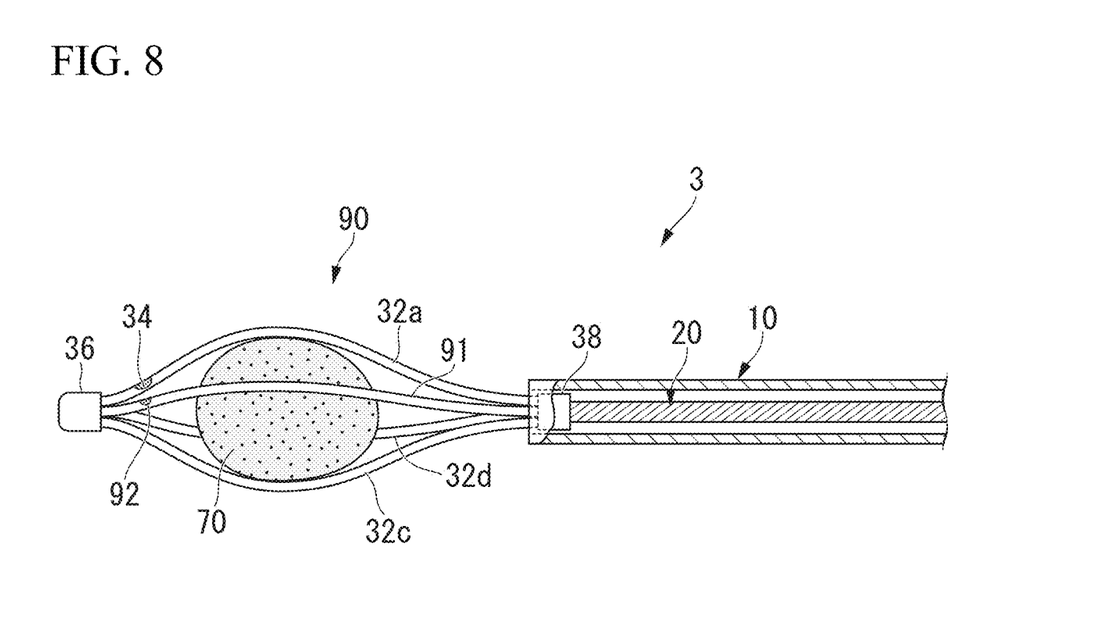
FIG. 8 is a view showing a motion of a second modification of the medical basket treatment tool according to the embodiment of the present invention when in use.
Figure 9:
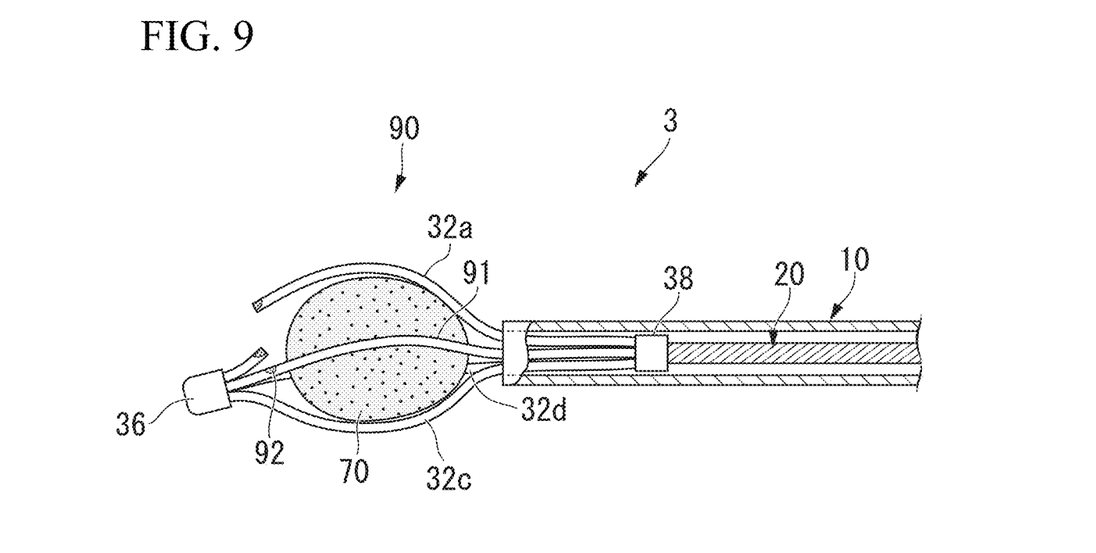
FIG. 9 is a view showing the motion of the second modification of the medical basket treatment tool according to the embodiment of the present invention when in use.
Figure 10:
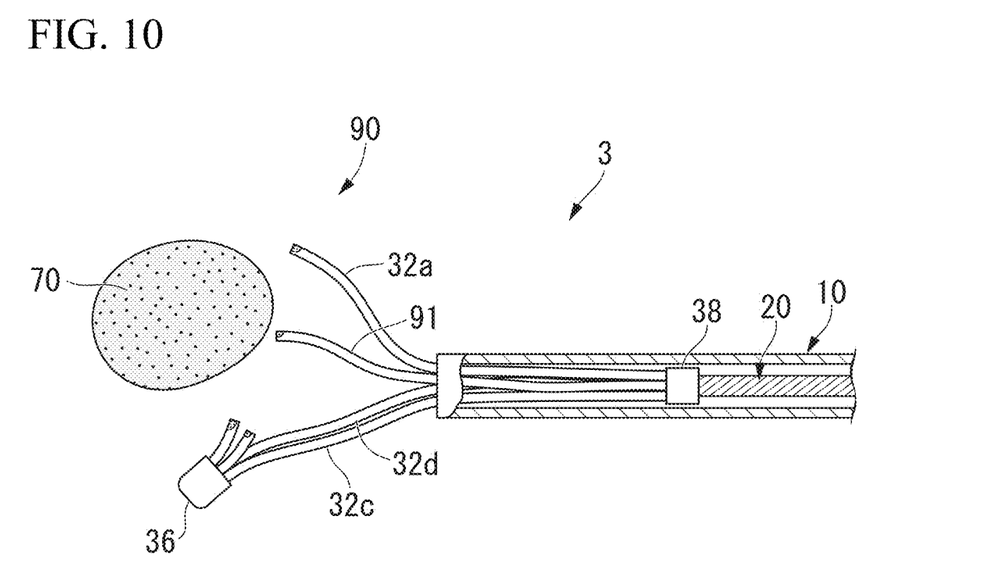
FIG. 10 is a view showing the motion of the second modification of the medical basket treatment tool according to the embodiment of the present invention when in use.

As a second modification of the medical basket treatment tool according to the present embodiment, a medical basket 3 is shown in FIG. 8 to FIG. 10. The medical basket 3 is different from the medical basket 1 in that, in addition to the fragile part 34 being provided for the basket wire 32a, a fragile part 92 is provided in the vicinity of the distal end tip 36 (at a position closer to a distal end of a basket unit 90 than a proximal end of the basket unit 90) on a basket wire 91. In comparison with the heat treatment for the fragile part 34, the fragile part 92 is subjected to heat treatment in which a laser is radiated with low irradiation fluence. For this reason, the fragile part 92 is formed in a range smaller than that of the fragile part 34. Therefore, tensile strength of the basket wire 91 (first tensile strength) on which the fragile part 92 is provided is less than tensile strength of the basket wires 32c and 32d on which the fragile part is not provided, but is greater than tensile strength of the basket wire 32a (second tensile strength) on which the fragile part 34 is provided. With regard to other constitutions, the medical basket 3 has the same constitution as the medical basket 1.

FIG. 8 to FIG. 10 are views showing a motion of the medical basket 3 when in use. FIG. 8 shows a state in which a foreign material 70 impacts the medical basket 3 and the foreign material 70 is not detached. In this state, when the manipulating wire 20 is pulled to the proximal end side and a force greater than or equal to the second tensile strength is applied to the basket unit 90, the fragile part 34 configured to be more easily broken than other parts by the heat treatment of the heating process is broken on the basket wire 32a first as shown in FIG. 9. However, even when the basket wire 32a is broken, the foreign material 70 may not be released from the basket unit 90 in some cases. In this case, when the manipulating wire 20 is further pulled to the proximal end side and a force greater than or equal to the first tensile strength is applied to the basket unit 90, the fragile part 92 configured to be more easily broken than other parts by the heat treatment of the heating process is broken on the basket wire 91 as shown in FIG. 10. Thereby, the foreign material 70 is released from the basket unit 90. At this time, since the distal end tip 36 is still coupled to the basket wires 32c and 32d, the distal end tip 36 is not left in the body of the patient.

Figure 11:
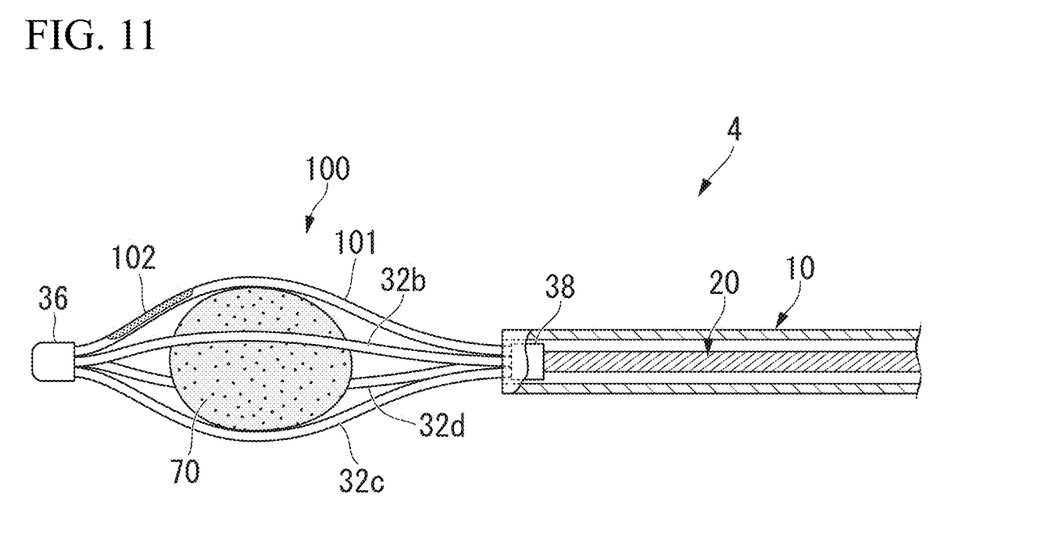
FIG. 11 is a view showing a motion of a third modification of the medical basket treatment tool according to the embodiment of the present invention when in use.
Figure 12:
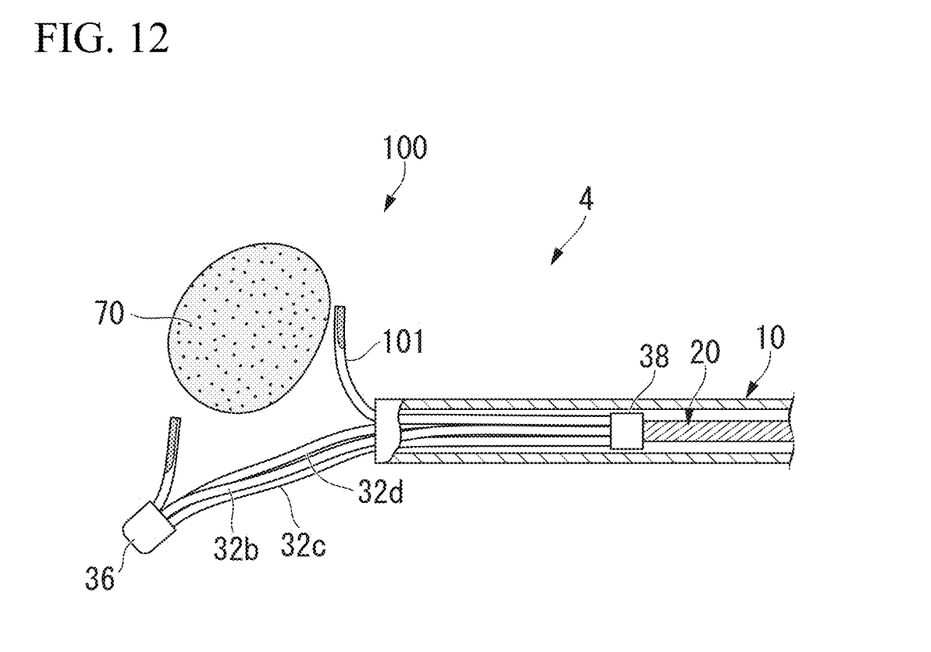
FIG. 12 is a view showing the motion of the third modification of the medical basket treatment tool according to the embodiment of the present invention when in use.

As a third modification of the medical basket treatment tool according to the present embodiment, a medical basket 4 is shown in FIG. 11 and FIG. 12. The medical basket 4 is different from the medical basket 1 in that, in place of the fragile part 34, a fragile part 102 is provided at a position closer to a proximal end of a basket unit 100 than a distal end of the basket unit 100 on a basket wire 101. The fragile part 102 is provided on the basket wire 101 in a range wider than that of the fragile part 34 at the proximal end side. With regard to other constitutions, the medical basket 4 has the same constitution as the medical basket 1.

FIG. 11 and FIG. 12 are views showing a motion of the medical basket 4 when in use. FIG. 11 shows a state in which a foreign material 70 impacts the medical basket 4 and the foreign material 70 is not detached. In this state, when the manipulating wire 20 is pulled to the proximal end side and a force greater than or equal to predetermined tensile strength is applied to the basket unit 100, the fragile part 102 configured to be more easily broken than other parts by the heat treatment of the heating process is broken at the basket wire 101 as shown in FIG. 12. Thereby, the foreign material 70 is released from the basket unit 100. At this time, since the distal end tip 36 is still coupled to the basket wires 32b, 32c and 32d, the distal end tip 36 is not placed in the body of a patient.

Figure 13:
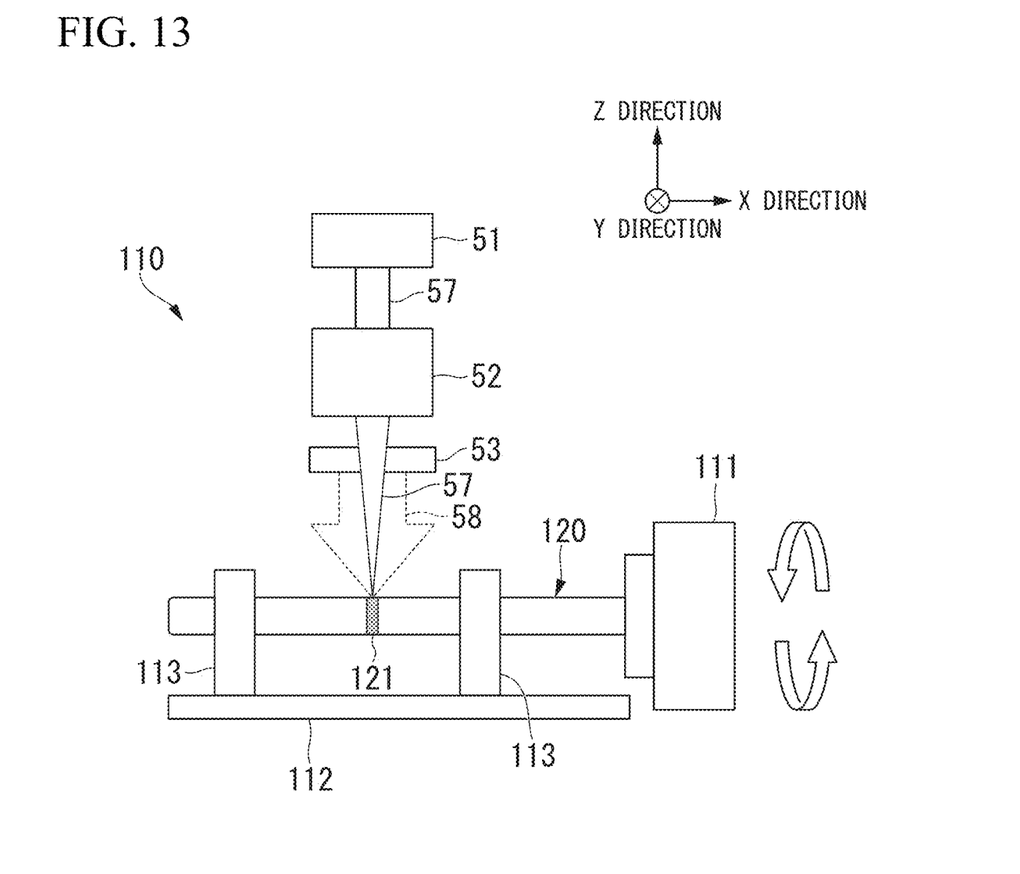
FIG. 13 is a view showing a modification of a laser heat treatment apparatus used in a heating process in the method for manufacturing a medical basket treatment tool according to the embodiment of the present invention.

The heating process of the method for manufacturing a medical basket treatment tool according to the present embodiment may be performed using a laser heat treatment apparatus 110 shown in FIG. 13. The laser heat treatment apparatus 110 is different from the laser heat treatment apparatus 50 in that, in place of the holder 54 and the stage 55, a holder 111 and a stage 112 are provided. The holder 111 holds a wire 120 that is a target on which a heating process is performed to be rotatable about an axis of the wire 120. The stage 112 includes supports 113, which support the wire 120 held by the holder 111 to be rotatable about the axis of the wire 120, on the top thereof. With regard to the other constitution, the laser heat treatment apparatus 110 has the same constitution as the laser heat treatment apparatus 50.

The heating process performed using the laser heat treatment apparatus 110 is different from the heating process performed using the laser heat treatment apparatus 50 in that a laser is irradiated on a target portion 121 while rotating the wire 120 about the axis of the wire 120. For this reason, when the laser heat treatment apparatus 110 is used in the heating process, the target portion 121 is provided throughout the wire 120 in a circumferential direction of the wire 120, and correspondingly the fragile part is formed throughout the wire in a circumferential direction of the wire. When the laser heat treatment apparatus 110 is used in the heating process, as the wire 120 is rotated, the influence of laser heating is different compared to when the laser heat treatment apparatus 50 is used, and thus the irradiation fluence is appropriately adjusted unlike the laser heat treatment apparatus 50. In this way, the heating process according to the present embodiment may be performed while rotating the wire 120. With regard to motions other than this, the heating process when the laser heat treatment apparatus 110 is identical to the heating process when the laser heat treatment apparatus 50 is used.

The shape of the target portion subjected to the heat treatment in the heating process is not limited to the foregoing, and an arbitrary shape such as a spiral shape may be adopted. The shape of the target portion may be appropriately set depending on the size, the shape, the number, and so on, of the foreign material collected by the medical basket treatment tool, and an intracorporal region on which a treatment is performed.

Next, examples of the heating process in the method for manufacturing a medical basket treatment tool according to the embodiment of the present invention will be described.

Example 1

In this example, a heating process was performed using the laser heat treatment apparatus 50 shown in FIG. 2. A wire formed using NiTi and having a diameter of 0.5 mm was used as a wire targeted for heat treatment. The tensile strength of this wire before the laser heat treatment was 350 N. In the laser heat treatment apparatus 50, the wavelength band of the laser 57 was set to 800 to 1100 nm, and a condensing lens having a focal length f of 100 mm was used as the condensing lens of the optical head 52. An argon gas was used as the gas 58. In this example, the heating process was performed by changing the irradiation fluence into three types of $2.1 \times 10^3$ J/cm$^2$, $4.1 \times 10^3$ J/cm$^2$, and $5.1 \times 10^3$ J/cm$^2$, and the tensile strength of the wire after the heating process was measured. In any case, the target portion of the wire was one place, and the number of times of the heat treatment is once. The measured results are shown in Table 1.

TABLE 1

| Irradiation fluence [J/cm$^2$] | Tensile strength [N] |
|---|---|
| (Before laser heat treatment) | 350 |
| 2.1 × 10$^3$ | 320 |
| 4.1 × 10$^3$ | 200 |
| 5.1 × 10$^3$ | 200 |

As shown in Table 1, in the case of any irradiation fluence, the tensile strength was reduced compared to 350 N that is the tensile strength before the laser heat treatment. Accordingly, it was confirmed that the tensile strength of the target portion of the wire was properly reduced by this heating process.

Example 2

In this example, a heating process was performed using the laser heat treatment apparatus 50 shown in FIG. 2. A wire formed using stainless steel containing 18 wt % Cr and 8.43 wt % Ni and having a diameter of 0.5 mm was used as a wire targeted for heat treatment. The tensile strength of this wire before the laser heat treatment was 380 N. In the laser heat treatment apparatus 50, the wavelength band of the laser 57 was set to 800 to 1100 nm, and a condensing lens having a focal length f of 100 mm was used as the condensing lens of the optical head 52. An argon gas was used as the gas 58. In this example, the heating process was performed by changing the irradiation fluence into three types of 2.1×10$^3$ J/cm$^2$, 4.1×10$^3$ J/cm$^2$, and 5.1×10$^3$ J/cm$^2$, and the tensile strength of the wire after the heating process was measured. In any case, the target portion of the wire was one place, and the number of times of the heat treatment is once. The measured results are shown in Table 2.

TABLE 2

| Irradiation fluence [J/cm$^2$] | Tensile strength [N] |
|---|---|
| (Before laser heat treatment) | 380 |
| 2.1 × 10$^3$ | 370 |
| 4.1 × 10$^3$ | 270 |
| 5.1 × 10$^3$ | 250 |

As shown in Table 2, in the case of any irradiation fluence, the tensile strength was reduced compared to 380 N that is the tensile strength before the laser heat treatment. Accordingly, it was confirmed that the tensile strength of the target portion of the wire was properly reduced by this heating process.

Example 3

In this example, a heating process was performed using the laser heat treatment apparatus 110 shown in FIG. 13. A wire formed using NiTi and having a diameter of 0.5 mm was used as a wire targeted for heat treatment. The tensile strength of this wire before the laser heat treatment was 350 N. In the laser heat treatment apparatus 110, the wavelength band of the laser 57 was set to 800 to 1100 nm, and a condensing lens having a focal length f of 100 mm was used as the condensing lens of the optical head 52. An argon gas was used as the gas 58. Further, the holder 111 was rotated at a rotating speed of 475 rpm. In this example, the heating process was performed by changing the irradiation fluence into five types of 1.0×10$^3$ J/cm$^2$, 2.1×10$^3$ J/cm$^2$, 3.1×10$^3$ J/cm$^2$, 4.1×10$^3$ J/cm$^2$, and 5.1×10$^3$ J/cm$^2$, and the tensile strength of the wire after the heating process was measured. In any case, the target portion of the wire was one place, and the number of times of the heat treatment is once. The measured results are shown in Table 3.

TABLE 3

| Irradiation fluence [J/cm$^2$] | Tensile strength [N] |
|---|---|
| (Before laser heat treatment) | 350 |
| 1.0 × 10$^3$ | 335 |
| 2.1 × 10$^3$ | 320 |
| 3.1 × 10$^3$ | 200 |
| 4.1 × 10$^3$ | 200 |
| 5.1 × 10$^3$ | 200 |

As shown in Table 3, in the case of any irradiation fluence, the tensile strength was reduced compared to 350 N that is the tensile strength before the laser heat treatment. Accordingly, it was confirmed that the tensile strength of the target portion of the wire was properly reduced by this heating process.

It was confirmed from the aforementioned results of Examples 1 to 3, if the irradiation fluence is at least 1.0×10$^3$ J/cm$^2$ in the heating process, the mechanical strength (the tensile strength) of the target portion of the wire can be properly reduced.

According to the method for manufacturing a medical basket treatment tool according to the embodiment of the present invention, the laser is irradiated on the target portion configured to be easily broken at the wire in the heating process, and thereby performs the heat treatment of heating the target portion. In the method for manufacturing a medical basket treatment tool according to the embodiment of the present invention, since only this target portion can be accurately heated with a predetermined irradiation fluence by using the laser, the mechanical strength of the target portion can be properly reduced by the heat treatment. Accordingly, in the method for manufacturing a medical basket treatment tool according to the embodiment of the present invention, the medical basket treatment tool capable of reliably breaking a part intended to be broken when an excessive force is applied in predetermined conditions can be manufactured.

In the method for manufacturing a medical basket treatment tool according to the present embodiment, as the heat treatment is performed in a gas atmosphere in the heating process, the gas is properly selected for the wire, and thereby a progress of an unnecessary chemical reaction such as oxidation of the wire can be prevented. Therefore, in the method for manufacturing a medical basket treatment tool according to the present embodiment, the mechanical strength of the target portion can be properly reduced by the heat treatment.

In the method for manufacturing a medical basket treatment tool according to the present embodiment, as the alloy of which the wire is formed is the shape-memory alloy containing Ni at 55.8 wt % or more and 56.0 wt % or less, the wire has biocompatibility, and thus a burden on a patient can be reduced.

In the method for manufacturing a medical basket treatment tool according to the present embodiment, when the alloy of which the wire is formed is the shape-memory alloy, a predetermined temperature in the heat treatment is preferably 550° C. or higher and 800° C. or lower. In the method for manufacturing a medical basket treatment tool according to the present embodiment, the heat treatment is performed such that the target portion is heated to a temperature within this temperature range, and thereby the tensile strength of the wire can be favorably reduced.

In the method for manufacturing a medical basket treatment tool according to the present embodiment, as the alloy of which the wire is formed is the stainless steel containing Cr at 16 wt % or more and 26 wt % or less and Ni at 4 wt % or more and 26 wt % or less, the wire has biocompatibility, and thus a burden on a patient can be reduced.

In the method for manufacturing a medical basket treatment tool according to the present embodiment, when the alloy of which the wire is formed is the stainless steel, a predetermined temperature in the heat treatment is preferably 600° C. or higher and 1000° C. or lower. In the method for manufacturing a medical basket treatment tool according to the present embodiment, the heat treatment is performed such that the target portion is heated to a temperature within this temperature range, and thereby the tensile strength of the wire can be favorably reduced.

As the method for manufacturing a medical basket treatment tool according to the present embodiment further includes the basket forming process of forming the medical basket using the wire having the target portion in addition to the heating process, the medical basket having the wire in which the mechanical strength is reduced by performing the heat treatment can be formed. Accordingly, in the medical basket treatment tool according to the present embodiment, when the foreign material causes impaction in this medical basket, the foreign material can be released, by breaking the wire.

In the method for manufacturing a medical basket treatment tool according to the present embodiment, the target portion is disposed at a position closer to the distal end of the basket unit than the proximal end of the basket unit in the basket unit of the medical basket in the basket forming process. Thereby, in the medical basket treatment tool according to the present embodiment, when the target portion is broken when in use, the length of the wire that has the broken portion that faces the proximal end side of the basket unit when in use can become short. Accordingly, in the medical basket treatment tool according to the present embodiment, when the medical basket is pulled to the proximal end side after being broken, the surrounding tissue can be prevented from being damaged at the broken end that faces the proximal end side of the basket unit.

According to the medical basket treatment tool according to the present embodiment, the laser is irradiated on the target portion of the wire, and thereby the target portion is heated. Thereby, the fragile part is formed. As the laser is used, only this target portion can be accurately heated with a predetermined irradiation fluence. For this reason, the mechanical strength of the target portion can be properly reduced by heating caused by the laser. Accordingly, in the medical basket treatment tool according to the present embodiment, the fragile part that is the target portion heated by the laser can be reliably broken when an excessive force is applied in predetermined conditions.

In the present embodiment, the constitutions of the laser heat treatment apparatus 50 and the laser heat treatment apparatus 110 are one example, and the present invention is not limited thereto. For example, a nozzle can be used as a method for injecting the gas 58, but a chamber or the like other than the nozzle may be used.

While preferred embodiments of the present invention have been described and shown above, it should be understood that these are exemplary of the invention and the present invention is not limited to these embodiments and modified examples thereof. Within a range not departing from the gist or spirit of the present invention, additions, omissions, substitutions, and other modifications to the constitution can be made.

The present invention is not to be considered as being limited by the foregoing description, and is limited only by the scope of the appended claims.

What is claimed is:

1. A method for manufacturing a medical basket treatment tool having one or more wires formed using an alloy containing two or more metals, the method comprising
    a heating process of performing heat treatment on a target portion of at least one wire among the wires one or more times, the heat treatment including irradiating the target portion with a laser with an irradiation fluence of $10^3$ J/cm$^2$ or more and heating the target portion to a predetermined temperature lower than a solid solubility limit of the alloy.

2. The method for manufacturing a medical basket treatment tool according to claim 1,
    wherein the heat treatment is performed in a gas atmosphere.

3. The method for manufacturing a medical basket treatment tool according to claim 1,
    wherein the alloy is a shape-memory alloy containing Ni at 55.8 wt % or more and 56.0 wt % or less.

4. The method for manufacturing a medical basket treatment tool according to claim 3,
    wherein the predetermined temperature of the heat treatment is 550° C. or higher and 800° C. or lower.

5. The method for manufacturing a medical basket treatment tool according to claim 1,
    wherein the alloy is stainless steel containing Cr at 16 wt % or more and 26 wt % or less and Ni at 4 wt % or more and 26 wt % or less.

6. The method for manufacturing a medical basket treatment tool according to claim 5,
    wherein the predetermined temperature of the heat treatment is 600° C. or higher and 1000° C. or lower.

* * * * *